United States Patent
Nakamori et al.

(12) 
(10) Patent No.: US 7,329,726 B2
(45) Date of Patent: Feb. 12, 2008

(54) PHYSIOLOGICALLY ACTIVE PEPTIDES

(75) Inventors: Shigeru Nakamori, Fukui-Ken (JP); Hiroshi Takagi, Fukui (JP); Masakazu Takahashi, Fukui-Ken (JP); Kazuhisa Tsujimoto, Fukui (JP); Hideyuki Yamada, Fukui (JP)

(73) Assignee: Seiren Kabushiki Kaisha, Fukui-Shi (JP)

( * ) Notice: Subject to any disclaimer, the term of this patent is extended or adjusted under 35 U.S.C. 154(b) by 0 days.

(21) Appl. No.: 11/010,800

(22) Filed: Dec. 13, 2004

(65) Prior Publication Data

US 2005/0196861 A1 Sep. 8, 2005

(30) Foreign Application Priority Data

Mar. 2, 2004 (JP) ............................. 2004-057584

(51) Int. Cl.
*C07K 7/06* (2006.01)
*A61K 38/08* (2006.01)
*C12N 5/02* (2006.01)

(52) U.S. Cl. ...................... 530/328; 514/15; 435/384; 435/405

(58) Field of Classification Search ...................... None
See application file for complete search history.

(56) References Cited

U.S. PATENT DOCUMENTS

2003/0134388 A1* 7/2003 Sasaki et al. .............. 435/69.1

FOREIGN PATENT DOCUMENTS

EP 1 302 544 4/2003

WO 02086133 A1 * 10/2002

OTHER PUBLICATIONS

Takahashi, M., et al. "The Silk Protein, Sericin, Protects Against Cell Death Caused by Acute Serum Deprivation in Insect Cell Culture" *Biotechnology Letters* (2003) vol. 25, No. 21, pp. 1805-1809 XP-002319987.
Terada, S., et al. "Sericin, a Protein Derived from Silkworms, Accelerates the Proliferation of Several Mammalian Cell Lines including a Hybridoma" *Cytotechnology*, (2002) vol. 40, No. 1-3, p. 3-12 XP009016457.
Database Registry, *STN* (2003) Database Accession No. 480131-96-2 XP-002319992.
Database Registry, *STN* (2003) Database Accession No. 492461-35-5 XP-002319993.
Database Registry, *STN* (2004) Database Accession No. 663900-19-4 XP-002319994.

* cited by examiner

*Primary Examiner*—Ruixiang Li
(74) *Attorney, Agent, or Firm*—Ladas and Parry LLP

(57) ABSTRACT

A peptide according to the present invention is selected from the group consisting of: (a) a peptide having the amino acid sequence represented by SEQ ID NO: 1; (b) a peptide having a modified amino acid sequence of the amino acid sequence described in (a) above, in which one or more amino acid residues are deleted, substituted, inserted or added, and having cell death-preventing activity and/or cell growth-promoting activity; and (c) a peptide which has an amino acid sequence having at least 80% homology with the peptide consisting of the amino acid sequence described in (a) above and has cell death-preventing activity and/or cell growth-promoting activity. The peptide has cell death-preventing activity and/or cell growth-promoting activity, is highly safe, and can be produced without difficulty. The peptide is useful as a culture supplement or as an effective component for a cell culture medium.

8 Claims, No Drawings

SEQUENCE LISTING

<160> NUMBER OF SEQ ID NOS: 3

<210> SEQ ID NO 1
<211> LENGTH: 10
<212> TYPE: PRT
<213> ORGANISM: ARTIFICIAL
<220> FEATURE:
<223> OTHER INFORMATION: Peptide derived from sericin

```
<400> SEQUENCE: 1

Ser Gly Gly Ser Ser Thr Tyr Gly Tyr Ser
1               5                   10

<210> SEQ ID NO 2
<211> LENGTH: 38
<212> TYPE: PRT
<213> ORGANISM: ARTIFICIAL
<220> FEATURE:
<223> OTHER INFORMATION: Peptide derived from sericin

<400> SEQUENCE: 2

Ser Ser Thr Gly Ser Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
                20                  25                  30

Ser Arg Asp Gly Ser Val
            35

<210> SEQ ID NO 3
<211> LENGTH: 76
<212> TYPE: PRT
<213> ORGANISM: ARTIFICIAL
<220> FEATURE:
<223> OTHER INFORMATION: Peptide derived from sericin

<400> SEQUENCE: 3

Ser Ser Thr Gly Ser Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
                20                  25                  30

Ser Arg Asp Gly Ser Val Ser Ser Thr Gly Ser Ser Ser Asn Thr Asp
            35                  40                  45

Ser Asn Ser Asn Ser Ala Gly Ser Ser Thr Ser Gly Gly Ser Ser Thr
    50                  55                  60

Tyr Gly Tyr Ser Ser Asn Ser Arg Asp Gly Ser Val
65                  70                  75
```

PHYSIOLOGICALLY ACTIVE PEPTIDES

CROSS REFERENCE TO RELATED APPLICATIONS

This application is based on and claims the benefit of priority from the prior Japanese Patent Application No. 2004-057584, filed on Mar. 2, 2004, the disclosure of which is incorporated herein by reference in its entirety.

BACKGROUND OF THE INVENTION

1. Field of the Invention

The present invention relates to physiologically active peptides having cell death-preventing activity and/or cell growth-promoting activity, and to medium supplements for cell culture containing the same.

2. Background Art

In animal cells, changes in culture conditions are known to cause marked cell growth reduction and cell death. Accordingly, components derived from a mammal, such as fetal calf serum and bovine serum albumin, is generally added to a medium for animal cell culture to improve the efficiency of cell growth.

However, there has been pointed out that the components derived from a mammal may carry a risk of being contaminated with viruses, pathogenic agents, and the like, which could be a major problem in safety. Therefore, use of media without components derived from a mammal has been so far suggested. However, use of these media occasionally causes marked cell growth reduction and cell death, which makes the cell culture difficult.

Accordingly, a method of adding a peptide which is components derived from a plant and has cell growth-promoting activity, such as a peptide derived from wheat, in place of components derived from a mammal, to a medium for animal cell culture has been suggested for the purpose of promoting cell growth. However, even with use of such components derived from a plant, sufficient effect has not necessarily been attained for certain kinds of cells or under certain culture conditions.

Accordingly, the present inventors previously found that the protein sericin, which can be extracted from natural silkworm cocoons or the like, has growth-promoting activity for animal cells and thus suggested to add sericin to a medium (International Publication WO 02/086133). The sericin contained an essential region consisting of 38 amino acids and other nonessential regions. Further, a sericin derivative at least containing the essential region was also capable of exhibiting growth-promoting activity for animal cells. Such growth-promoting activity for animal cells was similarly exhibited with sericin or a sericin derivative which was artificially synthesized by a chemical or genetic engineering method.

However, there are several kinds of sericin components contained in natural silkworm cocoons and the like, even limiting to those with different molecular weight. Further, various classes of molecules are to be contained in a sericin fraction obtained by extraction since the process for sericin extraction comprises hydrolysis. In order to purify a single component having a specific structure from a mixture of such various classes of molecules, complicated operations and enormous costs are generally required. Further, such a mixture may not be appropriate for use in the field of pharmaceuticals or tissue engineering because its safety to the body or its stability is often difficult to be fully secured.

It is generally known that the larger the molecular weight of the peptide, the more complicated the structure, which causes technical difficulties in chemical synthesis and purification. From the viewpoint of obtaining a necessary amount of a highly purified peptide, it is desirable for the peptide to have a molecular weight as small as possible while retaining desired activity.

On the other hand, in the case where a peptide is produced using genetic engineering techniques, a complicated operation in which a gene coding for a target peptide is prepared and introduced into a host cell is required. In order to obtain the target peptide from the inside of cells or culture supernatant, many purification steps are required, which increases production costs.

In the fields such as the production of useful substances and tissue engineering by cell culture, there is still a great need for culture medium components which are highly safe, capable of improving cell growth efficiency, and obtainable by relatively inexpensive chemical synthesis.

SUMMARY OF THE INVENTION

The present inventors have recently found that a peptide having a sequence consisting of 10 specific amino acids, which is a partial structure of a peptide having a sequence consisting of 38 amino acids corresponding to an essential region of naturally-derived sericin, alone exhibits excellent cell death-preventing activity and/or cell growth-promoting activity. In addition, this specific amino acid sequence is different from amino acid sequences of the serum components derived from mammals or peptides derived from plants, which are already known to enhance cell growth efficiency. Therefore, it was unexpected and surprising that a peptide according to the present invention can exhibit excellent cell death-preventing activity and/or cell growth-promoting activity. The present invention is based on these findings.

Accordingly, an objective of the present invention is to provide a peptide having cell death-preventing activity and/or cell growth-promoting activity, which is highly safe and easily produced.

The peptide according to the present invention is selected from the group consisting of the following (a) to (c):

(a) a peptide comprising the amino acid sequence represented by SEQ ID NO: 1, (b) a peptide comprising a modified amino acid sequence of the amino acid sequence described in (a) above, in which one or more amino acid residues are deleted, substituted, inserted or added, and having cell death-preventing activity and/or cell growth-promoting activity, and (c) a peptide which comprises an amino acid sequence having at least 80% homology with the peptide consisting of the amino acid sequence described in (a) above and has cell death-preventing activity and/or cell growth-promoting activity.

A supplement composition for cell culture medium according to the present invention comprises the peptide according to the present invention.

A cell culture medium according to the present invention at least comprises an effective amount of the peptide according to the present invention or the supplement composition for cell culture medium according to the present invention, and basal medium components.

A method for culturing cells according to the present invention comprises the step of maintaining or growing cells of interest by using a cell culture medium comprising an effective amount of the peptide according to the present invention or the supplement composition for cell culture medium according to the present invention.

According to the peptide of the present invention and the supplement composition for cell culture medium containing the peptide, the death of cells of interest can be prevented and the survival rate of the cells can be maintained or improved when cultured. Further, according to the peptide of the present invention and the supplement composition for cell culture medium containing the peptide, the growth of cells of interest can be promoted. Since the peptide according to the present invention comprises only about 10 amino acids, it can be obtained as a highly purified single peptide with ease and at a low cost.

Further, according to the peptide of the present invention, the safety of a culture product can be improved since serum components such as fetal calf serum or bovine serum albumin can be used in a reduced amount or its use can be totally avoided in cell culture. Further, since the peptide according to the present invention can be chemically synthesized with ease so that the risk of contamination with impurities commonly observed in the extraction from a natural product can be reduced, its safety can be sufficiently secured. Accordingly, the peptide according to the present invention is highly useful as a culture medium supplement or as an effective component of a cell culture medium.

Moreover, the peptide or the medium supplement composition according to the present invention can promote cell growth simply by adding it to a medium, which can reduce production costs in the production of animal cells for the purpose of tissue engineering and the production of useful substances by cell culture.

DETAILED DESCRIPTION OF THE INVENTION

Peptide

One embodiment of a peptide according to the present invention comprises the amino acid sequence represented by SEQ ID NO: 1. This amino acid sequence represented by SEQ ID NO: 1 is a part of the peptide consisting of 38 amino acids (SEQ ID NO: 2) disclosed in International Publication WO 02/086133 by the present inventors, and more specifically, corresponds to the amino acid sequence from 21 to 30 of the peptide. As far as the present inventors are aware, it has been completely unknown up to the present time that the fragment consisting of these specific 10 amino acids can exhibit excellent cell death-preventing activity and/or cell growth-promoting activity, with such a short fragment by itself.

The peptide according to the present invention includes not only one that is the same as the amino acid sequence represented by SEQ ID NO: 1 as mentioned above, but also one that comprises an amino acid sequence substantially the same as the one above. Namely, the peptide according to the present invention includes peptides of the following (b) and (c) in addition to the following (a) as mentioned above:

(a) a peptide comprising the amino acid sequence represented by SEQ ID NO: 1, (b) a peptide comprising a modified amino acid sequence of the amino acid sequence described in (a) above, in which one or more amino acid residues are deleted, substituted, inserted or added, and having cell death-preventing activity and/or cell growth-promoting activity, and (c) a peptide which comprises an amino acid sequence having at least 80% homology with the peptide consisting of the amino acid sequence described in (a) above and has cell death-preventing activity and/or cell growth-promoting activity.

All of the abovementioned peptides have cell death-preventing activity and/or cell growth-promoting activity.

In this specification, the term "peptide" also refers to a peptide derivative. The "peptide derivative" as used herein refers to one that exhibits the abovementioned cell death-preventing activity and/or cell growth-promoting activity and has modifications in which the amino group of the amino end (N-terminal) of the peptide or a part or all of the amino groups of individual amino acid side chains, and/or the carboxyl group of the carboxyl end (C-terminal) of the peptide or a part or all of the carboxyl groups of individual amino acid side chains, and/or a part or all of the functional groups of individual amino acid side chains of the peptide, other than amino groups and carboxyl groups, (for example, hydrogen groups, thiol groups, and amide groups) are substituted with other appropriate substituents (for example, phosphate groups). Such modifications with other appropriate substituents may be carried out for the purpose of, for example, protecting functional groups present in the peptide, improving the safety and tissue migration, or increasing the activity.

The "peptide derivative" also refers to a pharmaceutically acceptable salt of a peptide according to the present invention. Preferred examples of such a salt include alkali metal or alkaline-earth metal salts such as sodium salts, potassium salts, and calcium salts; salts with hydrogen halides, such as hydrofluorides, hydrochlorides, hydrobromides, and hydroiodides; salts with inorganic acids, such as nitrates, perchlorates, sulfates, and phosphates; salts with lower alkyl sulfonic acids, such as methane sulfonates, trifluoromethane sulfonates, and ethane sulfonates; salts with arylsulfonic acids, such as camphor sulfonates, benzene sulfonates, and p-toluene sulfonates; salts with organic acids, such as fumarates, succinates, citrates, tartrates, oxalates, maleates, acetates, malates, lactates, and ascorbates; and salts with amino acids, such as glycinates, phenylalanates, glutamates, and aspartates. Further, the peptide according to the present invention can be a solvate. Examples of such a solvate include hydrates, alcoholates (e.g., methanolates and ethanolates), and etherates (e.g., diethyl etherates).

In this specification, the term "amino acid" includes its optical isomers, namely both D and L forms. Further, the term "amino acid" as used herein may include not only 20 kinds of α-amino acids, which construct natural proteins, but also other α-amino acids as well as β-, γ- and δ-amino acids, and non-natural amino acids.

As used herein, the term "cell death-preventing activity" refers to a character capable of preventing the death or deterioration of cells of interest, and this "cell death-preventing activity" can maintain or improve the survival rate of the cells when cultured. Having "cell death-preventing activity" means being evaluated to have cell death-preventing activity, for example, when measured under conditions similar to those in Evaluation Test 1 in Example described later.

Further, the term "cell growth-promoting activity" refers to a character capable of promoting or maintaining growth of cells of interest, and this "cell growth-promoting activity" can increase or maintain the cell counts and cell density when cultured. Having "cell growth-promoting activity" means being evaluated to have cell growth-promoting activity, for example, when measured under conditions similar to those in Evaluation Test 2 in Example described later.

In (b) described above, the number of amino acid residues which may be deleted, substituted, inserted or added for the amino acid sequence represented by SEQ ID NO: 1 is preferably 1 to 5, more preferably 1 to 3, further more preferably 1 to 2, and most preferably 1.

According to a preferred embodiment of the present invention, the peptide of the abovementioned (b) is a peptide which comprises a modified amino acid sequence of the amino acid sequence described in (a) above, in which one or more amino acid residues are conservatively substituted, and has cell death-preventing activity and/or cell growth-promoting activity.

The term "conservative substitution" herein means substitution of one or more amino acid residues with other chemically homologous amino acid residues without substantially changing the activity of said peptide. For example, a certain hydrophobic residue can be substituted with another hydrophobic residue, or a certain polar residue can be substituted with another polar residue having the same charge. Functionally homologous amino acids that can be conservatively substituted in such a manner are known in the art for individual amino acids. More specifically, examples of nonpolar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of positively-charged (basic)amino acids include arginine, histidine, and lysine. Further, examples of negatively-charged (acidic) amino acids include aspartic acid and glutamic acid. Further, a peptide according to the present invention generally consists of polar (neutral) amino acids.

The peptide of the abovementioned (c) comprises an amino acid sequence having a homology of at least 80% with the peptide consisting of the amino acid sequence of the abovementioned (a) represented by SEQ ID NO: 1; the homology is preferably 90% or more.

Further, the figures for the homology given in this specification can be calculated using a homology search program known to those skilled in the art; for example, the figures can be easily calculated using default (preset option) parameters in FASTA, BLAST (Basic Local Alignment Search Tool), and the like.

Production of Peptide

A peptide according to the present invention can be produced by applying any known method. Since the peptide according to the present invention is a low molecular weight peptide (theoretical molecular weight of 965) basically consisting of 10 amino acids, it can be easily produced by any method which is known to those skilled in the art and commonly used for peptide synthesis.

Examples of such a synthesis method include a liquid phase method, solid phase method, and solid phase-liquid phase combination method, using the t-Boc method in which an α-amino group of an amino acid is protected by a t-butoxy carbonyl (Boc) group and a side chain functional group is protected by a benzyl alcohol type protecting group or the Fmoc method in which an α-amino group of an amino acid is protected by a 9-fluorenylmethoxycarbonyl (Fmoc) group and a side chain functional group is protected by a t-butyl alcohol type protecting group. Appropriate references for carrying out these methods may include "Peptide Synthesis" by Nobuo Izumiya et al., 1984, published by Maruzen; "Biochemistry Experimental Course (I)/Protein Chemistry" Vol. 4, edited by the Japanese Chemical Society, 208-495, 1977, published by Tokyo Kagaku Dojin; "New Biochemistry Experimental Course (I)/Protein" Vol. VI (Synthesis and Expression), edited by the Japanese Chemical Society, 3-74, 1992, published by Tokyo Kagaku Dojin; and "Development of Pharmaceuticals, Second Series 14/Peptide Synthesis", published by Hirokawa Shoten.

The peptide synthesized as mentioned above can be purified by an ordinary method to recover the target peptide according to the present invention. Examples of such a method for purification include ion exchange chromatography, reversed phase liquid chromatography, and affinity chromatography. These methods may be used alone or in combination. The synthesized peptide is purified in this manner to obtain the peptide according to the present invention as a highly purified single peptide. The resulting peptide may be dried, if necessary, further by freeze-drying or other means.

The amino acid sequence of the peptide thus obtained can be analyzed and confirmed using a protein sequencer, which reads an amino acid sequence from the N-terminal end by the Edman sequencing analysis, FAB-MS, TOF-MS or the like.

Thus, according to one preferred embodiment of the present invention, the peptide according to the present invention is obtained by chemical synthesis.

Further, a peptide according to the present invention may be produced, for example, using genetic engineering techniques. Namely, in case where a DNA encoding an amino acid sequence representing the peptide of the present invention is available or can be constructed, the peptide of the present invention can be produced in the transformed cell obtained by transforming a host cell with such a DNA. Namely, the peptide according to the present invention can be produced by obtaining a DNA, in particular in a form of a recombinant vector, which comprises a DNA fragment encoding an amino acid sequence representing the peptide in an expressible state and is replicable in a host cell, transforming a host cell using the DNA or the vector, and culturing the transformant thus obtained. Here, a so-called host-vector system may be used for the production of said peptide. In applying such a host-vector system, various methods for constructing expression vectors (recombinant vectors) and transformation methods commonly used in this field of technology can be used.

Supplement Composition for Culture Medium

A supplement composition for cell culture medium according to the present invention comprises a peptide according to the present invention. Accordingly, the supplement composition for cell culture medium according to the present invention comprises a peptide according to the present invention, and may further contain an optional component as long as it doesn't interfere with the activity of the said peptide. Examples of such an optional component include a part of commonly used medium components (e.g., vitamins, hormones) and components known in the pharmaceutical field. Examples of such components known in the pharmaceutical field include those generally used, such as an excipient, filling agent, disintegrator, binding agent, lubricant, coloring agent, diluent, wetting agent, surfactant, dispersing agent, buffering agent, preservative, dissolution agent, antiseptic, flavoring agent, analgesic agent, and stabilizer. Further, pH controlling agent, isotonizing agent and the like can also be used as the abovementioned components. These components can be used as a pharmaceutically acceptable carrier in the present invention.

The dosage form of the supplement composition for culture medium according to the present invention is not particularly limited; examples of the typical dosage form include a capsule, powder, granule, solid, liquid, gel, and sheet. They can be produced appropriately using any of the components mentioned above.

The amount of the supplement composition for culture medium according to the present invention to be used can be appropriately changed so as to attain the desired concentration of a peptide according to the present invention in the supplemented medium.

Cell Culture Medium

A cell culture medium according to the present invention at least comprises an effective amount of a peptide according to the present invention or a supplement composition for cell culture medium according to the present invention and basal medium components.

In the present invention, the basal medium components generally comprises carbon sources assimilatable by animal cells, digestible nitrogen sources and inorganic salts, which include sugars, amino acids, inorganic salts, vitamins and the like. If necessary, a trace nutritionally stimulating substance and a trace effective substance, such as a precursor, can be included in the basal medium components.

Any medium components known to those skilled in the art can be used as such basal medium components; specific examples include MEM medium (H. Eagle, *Science*, 130, 432 (1959)), DMEM medium (R. Dulbecco, *Virology*, 8, 396 (1959)), RPMI1640 medium (G. E. More, *J.A.M.A.*, 199, 519, (1967)), Ham's F12 medium (R. G. Ham, *Proc. Natl. Acad. Sci., U.S.A.*, 53, 288 (1965)), MCDB104 medium (W. L. Mckeehan, *In Vitro*, 13, 399 (1977)), MCDB153 medium (D. M. Peehe, *In Vitro*, 16, 526 (1980)), and Sf900IISFM medium (e.g., Invitrogen).

Also other media, such as serum-free medium ASF104 (Ajinomoto), serum-free medium SF-02 (Sanko Junyaku Co., Ltd.), serum-free medium Hybridoma-SFM (Lifetech Oriental), serum-free medium BIO-MPM-1 (Biological Industries), serum-free medium EX-CELL™ 302-HDP (JRH Biosciences), serum-free medium Cosmedium 001 (Cosmo Bio), and serum-free medium SFM-101 (Nissui Pharmaceutical Co., Ltd.), can be appropriately used in the present invention.

A cell culture medium according to the present invention may, if necessary, contain various cell growth factors, for example, binding proteins such as albumin and transferrin, hormones such as insulin, epithelial growth hormone (EGF), fibroid cell growth factor and various steroid hormones, and cell adhesive factors such as fibronectin, as well as serum, as long as the abovementioned components are included.

According to a preferred embodiment of the present invention, the cell culture medium is preferably a medium containing serum in a smaller amount as compared to commonly used media, and more preferably a serum-free medium, namely a medium containing substantially no serum-derived component. Here the serum-free medium is a medium which contains substantially no serum and may contain cell growth factors and hormones other than serum.

According to one embodiment of the present invention, there is provided a method of producing a cell culture medium which comprises the step of adding a peptide according to the present invention or a supplement composition for cell culture medium according to the present invention to basal medium components.

The amount of the peptide according to the present invention or the supplement composition for culture medium according to the present invention to be added to a cell culture medium can be appropriately changed depending on the kind of cells to be cultured and the culture conditions. When converted to the amount of the peptide according to the present invention to be added, the amount of the peptide contained in the total volume of medium is preferably 10-3000 mg/L, more preferably 50-2000 mg/L, and most preferably 100-1000 mg/L.

The present invention exhibits a sufficient effect even with a small content of the peptide of the present invention in the medium according to the present invention; however, the peptide of the present invention may be added in large amounts without causing any substantial problems since it is nontoxic and highly soluble in water.

The cell culture medium according to the present invention is preferably used for animal cell culture. The term "animal" as used herein includes mammals, fishes, avians, and insects.

Animal cells which can be cultured in the medium according to the present invention are not particularly limited and can be either cells of established cell lines or non-established normal cells obtained from biological tissues. Accordingly, animal cells in the present invention can be, for example, cells capable of producing proteins by themselves, cells transformed by genetic engineering to express heterologous proteins, or cells infected with various virus vectors.

Examples of the cells capable of producing proteins by themselves include hybridoma cells producing monoclonal antibodies, leucocytes producing interferon (IFN)-$\alpha$, fibroblasts producing IFN-$\beta$, lymphocytes producing IFN-$\gamma$, human kidney cells producing pro-urokinase (pro-UK) or UK, melanoma cells producing tissue plasminogen activator (tPA), In-111 cells producing insulin, HIT cells producing glucagon, HepG2 cells producing erythropoietin, and B151K12 cells producing interleukin-5.

Examples of the cells of established cell lines transformed by genetic engineering include Vero cells, HeLa cells, CHO (Chinese hamster ovary) cells, HKG cells, NIH3T3 cells, BHK cells, COS-1 cells, COS-7 cells, and myeloma cells.

Examples of the cells infected with virus vectors include those infected with virus vectors, such as retrovirus vectors, lentivirus vectors, adenovirus vectors, adeno-satellite virus vectors, and herpes virus vectors. These virus vectors can be genetically recombined by a commonly used genetic engineering method. Further, examples of the animal cells to be infected with these virus vectors and cultured using the medium of the present invention include HEK (human embryonic kidney) 293 cells, A549 cells, and PER.C6 cells.

Culture Method and Others

According to another preferred embodiment of the present invention, there is provided a method for culturing cells which comprises the step of maintaining or growing cells of interest by using a cell culture medium comprising an effective amount of a peptide according to the present invention or a supplement composition for cell culture medium according to the present invention.

Culture conditions for this method, such as the oxygen concentration, osmotic pressure, pH, and temperature of the medium, can be appropriately changed depending on the kind of the cells to be cultured, the purpose of the culture, the volume of the culture, the kind of the basal medium components and the like. Any culture system, such as batch culture, continuous culture or circumfusion culture, can be used. High density culture can also be used.

According to still another embodiment of the present invention, there is provided a method of producing a protein, comprising the steps of adding an effective amount of a peptide of the present invention or a medium supplement composition of the present invention to a cell culture medium, culturing and growing animal cells capable of producing the protein using the medium thus obtained, and recovering the produced protein from said medium and/or said animal cells. Examples of the protein which can preferably be produced in this method of producing a protein include monoclonal antibodies, IFN-α, IFN-β, INF-γ, pro-UK or UK, tPA, insulin, glucagon, erythropoietin, and interleukin-5.

According to another embodiment of the present invention, there is provided a method of replicating a virus vector, which comprises the steps of adding an effective amount of a peptide of the present invention or a medium supplement composition of the present invention to a cell culture medium, culturing and growing animal cells infected with the virus vectors using the medium thus obtained and recovering the produced virus vectors from said medium and/or said animal cells. Virus vectors replicable by this method can be various virus vectors exemplified above and can be those created by genetic recombination, if necessary. Appropriately selected animal cells can be infected with the virus vectors of interest using a commonly used method. Further, the virus vectors can be recovered from grown cells by isolation and purification using various commonly used isolation methods such as ultrafiltration and centrifugation. Here it is desirable to appropriately select the method of recovering virus vectors depending on the kind of the virus vectors.

Generally, gene therapies are categorized into two kinds, i.e., ex vivo gene therapy and in vivo gene therapy. The former is a therapeutic method in which cells derived from a patient are first cultured outside the body and then treated for gene transfer, after which the resulting cells are administered to the patient; the latter is a therapeutic method in which gene-transferred vectors are directly introduced into the patient's body. According to the present invention, such gene-transferred virus vectors used for gene therapy can be replicated more efficiently than in a conventional method. Further, the medium according to the present invention exhibits an excellent growth promoting effect on animal cells used for such a replication method, such as 293 cells.

According to another embodiment of the present invention, there is provided use of a peptide according to the present invention for preventing cell death or promoting cell growth of cells of interest in cell culture.

According to still another embodiment of the present invention, there is provided use of a peptide according to the present invention for producing a cell culture medium.

EXAMPLE

The present invention is further illustrated by the following examples that are not intended as a limitation of the invention.

Production Example

Peptide A (the Present Invention)

A peptide comprising the amino acid sequence represented by SEQ ID NO: 1 was synthesized according to the Fmoc method using a peptide synthesizer Model 432A (Synergy (trade mark)) (Applied Biosystems).

Namely, 25 μmol of Fmoc-L-serine (tBu) HMP resin having p-hydroxymethyl-phenoxy-methyl (HMP) as a matrix and Fmoc amino acid cartridges for essential residues, each containing 75 μmol, were loaded on a peptide synthesizer and synthesis was carried out to obtain a peptide-bound resin. This resin was transferred into a centrifuge tube and treated with trifluoroacetic acid in the presence of thioanisole and ethanediol to cleave the peptide binding to the resin. Next, methyl-t-butyl ether (MTBE) was added and the peptide released from the resin was precipitated. The resulting precipitate was filtered with a filter while washing with MTBE to remove salts such as protecting groups and thus a peptide-containing fraction was obtained. Next, this peptide-containing fraction was dissolved and extracted using 2 M acetic acid to obtain a crude peptide. This crude peptide was purified by reverse-phase HPLC using a COSMOSIL $5C_{18}$-AR-II column (Nakarai Tesque). Here, 0.1% trifluoroacetic acid/water and 0.1% trifluoroacetic acid/acetonitrile were used as solvents. A peptide eluted from the column with acetonitrile was freeze-dried and about 5 mg of a purified peptide powder (peptide A) was obtained.

The peptide thus obtained was analyzed using a protein sequencer Procise NT (Applied Biosystems) and a MALDI-TOF-MS Voyager (trade mark) (Applied Biosystems) to confirm that this peptide had the amino acid sequence represented by SEQ ID NO: 1.

Peptide B (Comparative Example)

As described in Production Example 2 of International Publication WO 02/086133, a peptide having the amino acid sequence represented by SEQ ID NO: 3 (peptide B), which comprises 2 repeats of the sequence consisting of 38 amino acids contained in natural sericin (SEQ ID NO: 2), was obtained.

Evaluation Test

Evaluation Test 1: Cell Death-Preventing Activity

Cell death-preventing activity of the peptide according to the present invention was evaluated using an insect cell Sf9 (Invitrogen).

The Sf9 cell is usually subcultured using an Sf900IISFM medium (Invistrogen) containing 10% FCS (fetal calf serum) (Sigma) at a temperature of 27.5° C. It is known that marked cell death occurs when the Sf9 cells thus cultured are abruptly transferred into a medium without FCS and thus exposed to drastic serum-deprived conditions. In this test, cells to be tested were exposed under such drastic serum-deprived conditions and their survival rate was measured to evaluate cell death-preventing effect of the peptide according to the present invention.

First, Sf9 cells subcultured using a medium supplemented with 10% FCS were centrifuged at 1000 rpm at 4° C. for 5 minutes. Next, the supernatant was removed and the precipitated cells were suspended in an Sf900IISFM medium without FCS. The suspension was recentrifuged at 1000 rpm at 4° C. for 5 minutes to wash the cells.

Next, in order to expose the cells under drastic serum-deprived conditions, the washed cells were resuspended in an Sf900IISFM medium without FCS and a cell suspension having a cell density of $5 \times 10^5$ cells/ml was prepared.

On the other hand, peptide A (the present invention) was dissolved in an Sf900IISFM medium without FCS and peptide solutions were prepared at peptide concentrations of 0.2 mg/ml, 0.6 mg/ml, and 2.0 mg/ml. The peptide solutions thus prepared were sterilized by filtration.

Next, 50 μl of the abovementioned cell suspension and 50 μl each of the abovementioned peptide solutions were dispensed on a 96-well cell culture plate at a final cell density of $2.5 \times 10^5$ cells/ml and final peptide concentrations of 0.1 mg/ml, 0.3 mg/ml, and 1.0 mg/ml, respectively. This culture plate was incubated at 27.5° C. for 5 days.

After 5 days of incubation, cells were stained with Trypan blue and the number of dead cells and the number of viable cells were counted to obtain the survival rate. Here the survival rate means the ratio of the viable cell count to the total cell count upon cell counting.

As a comparative example, an experiment was carried out in the same manner as described above for peptide A, except that peptide B was used in place of peptide A (the present invention), to obtain the survival rate.

As another comparative example, an experiment was carried out in the same manner as described above for peptide A, except that a bovine serum albumin (Sigma) solution was used in place of the abovementioned peptide solutions, to obtain the survival rate.

The results are shown in Table 1.

When no peptide was added (no supplement), the survival rate of Sf9 cells was about 20%. On the other hand, in case where peptide A (the present invention) was added, the survival rate was markedly improved such that the cell survival rate was about 60% when the peptide concentration was 1.0 mg/ml. Further, the survival rate with peptide A (the present invention) was higher than that with peptide B (comparative example).

TABLE 1

| Sample | Sample concentration (mg/ml) | Survival rate (%) Average ± Standard deviation (n = 4) |
| --- | --- | --- |
| No supplement | 0 | 20.1 ± 2.8 |
| Peptide A (the present invention) | 0.1 | 28.5 ± 3.4 |
| | 0.3 | 47.3 ± 2.9 |
| | 1.0 | 58.0 ± 3.2 |
| Peptide B | 0.3 | 46.1 ± 2.2 |
| Bovine serum albumin | 0.3 | 62.5 ± 3.0 |

Evaluation Test 2: Cell Growth-Promoting Activity

Cell growth-promoting activity of the peptide according to the present invention was evaluated using an insect cell Sf9 (Invitrogen).

It is known that marked cell death as shown in Evaluation Test 1 and thereafter a decrease in cell growth occur when the Sf9 cells are exposed to drastic serum-deprived conditions. In this test, the cells to be tested were exposed under such drastic serum-deprived conditions and their growth ability was measured to evaluate cell growth-promoting effect of the peptide according to the present invention.

A cell suspension was prepared in the same manner as in Evaluation test 1, and peptide solutions were prepared using peptide A (the present invention) as in Evaluation test 1. Next, 50 µl of this cell suspension and 50 µl each of the peptide solutions were dispensed on a 96-well cell culture plate in the same manner as in Evaluation test 1, and this culture plate was incubated at 27.5° C. for 9 days.

After 9 days of incubation, cell growth-promoting effect was evaluated by the MTT assay.

Specifically, to each well of the 96-well plate incubated for 9 days was added 5 µl of 5 mg/ml 3-(4,5-dimethyl-2-thiazolyl)-2,5-diphenyl tetrazolium bromide (MTT) in phosphate-buffered physiological saline, and the plate was incubated at 27.5° C. for further 5 hours. During this culture process, MTT is transformed into insoluble formazan in viable cells. After 5 hours of incubation, cell culture supernatant was completely removed and then 200 µl each of a 10 mM $NH_4Cl$ solution with 10% SDS was added to each well to completely dissolve the cells and formazan in the cells. Next, the absorption coefficient at 595 nm was measured for each well using a microplate reader.

As a comparative example, an experiment was carried out in the same manner as the one with the abovementioned peptide A, except that peptide B was used in place of peptide A (the present invention), and then the absorption coefficient at 595 nm was measured for each well.

As another comparative example, an experiment was carried out in the same manner as described above for peptide A, except that a bovine serum albumin (Sigma) solution was used in place of the abovementioned peptide solutions, and then the absorption coefficient at 595 nm was measured for each well.

The results are shown in Table 2. Here the value of the absorption coefficient in the NTT assay increases with an increase in viable cell density.

When no peptide was added (no supplement), the absorption coefficient (OD 595 nm) by the NTT assay was about 0.3. On the other hand, in case where peptide A (the present invention) was added, the absorption coefficient by the NTT assay was markedly increased up to about 0.9 when the peptide concentration was 1.0 mg/ml. Further, the cell growth-promoting activity with peptide A (the present invention) was higher than that with peptide B (comparative example).

TABLE 2

| Sample | Sample concentration (mg/ml) | OD 595 nm Average ± Standard deviation (n = 4) |
| --- | --- | --- |
| No supplement | 0 | 0.30 ± 0.02 |
| Peptide A (the present invention) | 0.1 | 0.48 ± 0.01 |
| | 0.3 | 0.80 ± 0.02 |
| | 1.0 | 0.92 ± 0.02 |
| Peptide B | 0.3 | 0.72 ± 0.03 |
| Bovine serum albumin | 0.3 | 0.90 ± 0.03 |

The invention claimed is:

1. An isolated peptide consisting of the amino acid sequence of SEQ ID NO:1, said peptide having cell survival-increasing activity, cell growth-promoting activity or both.

2. The peptide according to claim 1, which is obtainable by chemical synthesis.

3. A supplement composition for cell culture medium, comprising the peptide of claim 1.

4. A cell culture medium comprising an effective amount of the peptide of claim 1 and basal medium components wherein the amount of the peptide contained in the total volume of the cell culture medium is 10-3000 mg/L.

5. The cell culture medium according to claim 4, which is for use in animal cell culture and is substantially free of serum-derived components.

6. A method for culturing cells, which comprises maintaining or growing cells of interest in a cell culture medium comprising an effective amount of the peptide of claim 1 and basal medium components, wherein the amount of the peptide contained in the total volume of the cell culture medium is 10-3000 mg/L.

7. The method according to claim 6, wherein the cells to be cultured are animal cells and the cell culture medium is substantially free of serum-derived components.

8. A method of producing a cell culture medium, which comprises the step of adding the peptide of claim 1 to basal medium components.

* * * * *